United States Patent [19]

Kölling et al.

[11] 3,950,395

[45] Apr. 13, 1976

[54] BENZOYLPHENYLGUANIDINES

[75] Inventors: Heinrich Kölling, Haan; Arno Widdig, Blecher; Herbert Thomas; Hans Peter Schulz, both of Wuppertal, all of Germany

[73] Assignee: Bayer Aktiengesellschaft, Germany

[22] Filed: Jan. 28, 1974

[21] Appl. No.: 437,045

[30] Foreign Application Priority Data

Feb. 1, 1973 Germany............................. 2304764

[52] U.S. Cl....... 260/471 C; 260/347.4; 260/465 D; 260/481 C; 260/553 A; 260/558 A; 424/285; 424/300
[51] Int. Cl.²........................................ C07C 133/10
[58] Field of Search..................... 260/471 C, 465 D

[56] References Cited
UNITED STATES PATENTS 3,828,094  8/1974  Widdig et al.................... 260/471 C Primary Examiner—James A. Patten

[57] ABSTRACT

Benzoylphenylguanidines of the formula

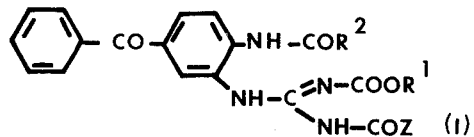

wherein
$R^1$ is alkyl of 1 to 4 carbon atoms;
$R^2$ is hydrogen; alkyl of 1 to 18 carbon atoms unsubstituted or substituted by one or more substituents selected from the group consisting of halogen, cyano, alkoxy of 1 to 4 carbon atoms, alkoxycarbonyl of 2 to 5 carbon atoms, phenoxy, halophenoxy, alkylphenoxy and alkoxyphenoxy; cycloalkyl of 5 to 8 carbon atoms; aralkyl unsubstituted or substituted by one or more substituents selected from the group consisting of halogen, alkyl of 1 to 4 carbon atoms and alkoxy of 1 to 4 carbon atoms; aryl unsubstituted or substituted by one or more substituents selected from the group consisting of halogen, alkyl of 1 to 4 carbon atoms and alkoxy of 1 to 4 carbon atoms;
Z is $OR^1$ wherein $R^1$ is as above defined or
$R^3$ wherein $R^3$ is hydrogen; alkyl of 1 to 18 carbon atoms unsubstituted or substituted by one or more substituents selected from the group consisting of halogen, cyano, alkoxy of 1 to 4 carbon atoms, alkoxycarbonyl of 2 to 5 carbon atoms, phenoxy, halophenoxy, alkylphenoxy and alkoxyphenoxy; alkenyl of 2 to 12 carbon atoms; alkinyl of 2 to 12 carbon atoms; cycloalkyl of 5 to 8 carbon atoms; aralkyl unsubstituted or substituted by one or more substituents selected from the group consisting of halogen, alkyl of 1 to 4 carbon atoms and alkoxy of 1 to 4 carbon atoms; aryl unsubstituted or substituted by one or more substituents selected from the group consisting of halogen, alkyl of 1 to 4 carbon atoms and alkoxy of 1 to 4 carbon atoms;

are useful for their anthelmintic activity.

22 Claims, No Drawings

BENZOYLPHENYLGUANIDINES

The present invention relates to benzoylphenylguanidines, a process for their production, anthelmintic compositions wherein said compounds are the active agent, and the methods of treating helmintic infections in humans and animals utilizing said compounds as the active agent.

Phenylguanidines of the formula

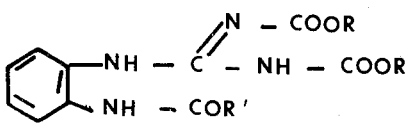

wherein
R is lower alkyl and
R' is either lower alkyl or hydrogen,
are known to exhibit anthelmintic activity (see German Offenlegungsschrift No. 2,117,293). However, the level of anthelmintic activity and the breadth of spectrum of activity are not as great or as broad as is desirable.

The present invention thus comprises compounds which were substantially more active than the known phenylguanidines. More particularly, the compounds of the present invention are benzoylphenylguanidines of the formula

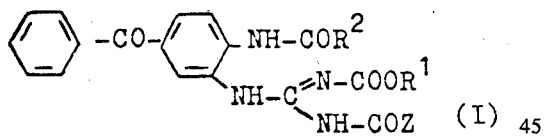

wherein
$R^1$ is alkyl of 1 to 4 carbon atoms;
$R^2$ is hydrogen; alkyl of 1 to 18 carbon atoms, especially lower alkyl, unsubstituted or substituted by 1 or more, especially 1, substituents selected from the group consisting of halogen, cyano, alkoxy of 1 to 4 carbon atoms, alkoxycarbonyl of 2 to 5 carbon atoms, phenoxy, halophenoxy, alkylphenoxy, especially lower alkylphenoxy, and alkoxyphenoxy, especially lower alkoxyphenoxy; cycloalkyl of 5 to 8 carbon atoms; aralkyl, especially benzyl, unsubstituted or substituted by 1 or more, especially 1, substituents selected from the group consisting of halogen, alkyl or 1 to 4 carbon atoms and alkoxy of 1 to 4 carbon atoms; aryl, especially monoaryl, and particularly phenyl, unsubstituted or substituted by 1 or more, especially 1, substituents selected from the group consisting of halogen, alkyl of 1 to 4 carbon atoms and alkoxy of 1 4 carbon atoms; 1-furyl; or —NR''R''' wherein R'' is hydrogen or alkyl of 1 to 4 carbon atoms;
R''' is hydrogen; alkyl of 1 to 18 carbon atoms, especially lower alkyl, and particularly alkyl of 1 to 4 carbon atoms, unsubstituted or substituted by 1 or more, especially 1, substituents selected from the group consisting of halogen, cyano, alkoxy of 1 to 4 carbon atoms and alkoxycarbonyl of 1 to 5 carbon atoms in the alkoxy moiety; cycloalkyl of 5 to 8 carbon atoms; aralkyl, especially benzyl, unsubstituted or substituted in the aryl portion by 1 or more, especially 1, substituents selected from the group consisting of halogen, alkyl of 1 to 4 carbon atoms and alkoxy of 1 to 4 carbon atoms; phenyl unsubstituted or substituted by 1 or more, especially 1, substituents selected from the group consisting of halogen, alkyl of 1 to 4 carbon atoms and alkoxy of 1 to 4 carbons; acyl of 1 to 18 carbon atoms unsubstituted or substituted by 1 or more, especially 1, substituents selected from the group consisting of halogen and alkoxy of 1 to 4 carbon atoms; aroyl, especially benzoyl, unsubstituted or substituted by 1 or more, especially 1, substituents selected from the group consisting of halogen, alkyl of 1 to 4 carbon atoms and alkoxy of 1 to 4 carbon atoms; alkylsulphonyl of 1 to 18 carbon atoms; arylsulphonyl, especially phenylsulphonyl, unsubstituted or substituted by 1 or more, especially 1, substituents selected from the group consisting of halogen, amino, alkyl of 1 to 4 carbon atoms and alkoxy of 1 to 4 carbon atoms; or dialkylamino of 1 to 4 carbon atoms in each alkyl moiety; or R'' and R''' together with the nitrogen atom to which they are attached form a 4- to 7-membered heterocyclic ring wherein the nitrogen atom is the only heteroatom or wherein oxygen, sulphur or oxygen and sulphur are also present as ring members; and Z is $OR^1$ wherein $R^1$ is as above defined, or, Z is $R^3$ wherein $R^3$ is hydrogen; alkyl of 1 to 18 carbon atoms, especially lower alkyl, unsubstituted or substituted by 1 or more, especially 1, substituents selected from the group consisting of halogen, cyano, alkoxy of 1 to 4 carbon atoms, alkoxy carbonyl of 2 to 5 carbon atoms, phenoxy, halophenoxy, alkylphenoxy, especially lower alkylphenoxy, and alkoxyphenoxy, especially lower alkoxyphenoxy; alkenyl of 2 to 12 carbon atoms, especially 2 to 4 carbon atoms; alkinyl of 2 to 12 carbon atoms, especially 2 to 4 carbon atoms; cycloalkyl of 5 to 8 carbon atoms; aralkyl, especially benzyl, unsubstituted or substituted by 1 or more, especially 1, substituents selected from the group consisting of halogen, alkyl of 1 to 4 carbon atoms and alkoxy of 1 to 4 carbon atoms; aryl, especially monoaryl, and particularly phenyl, unsubstituted or substituted by 1 or more, especially 1, substituents selected from the group consisting of halogen, alkyl of 1 to 4 carbon atoms and alkoxy of 1 to 4 carbon atoms; or 1-furyl.

The benzoylphenylguanidines of the present invention may be produced by reacting a 2-amino-4-benzoyl-aniline derivative of the formula:

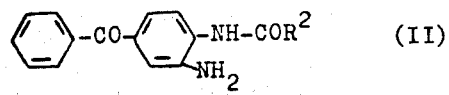

wherein $R^2$ is as above defined, with an isothiourea of the formula:

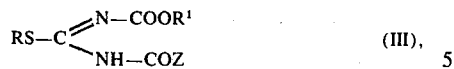

wherein $R^1$ and Z are as above defined, and R is alkyl of 1 to 4 carbon atoms, in the presence of a suitable diluent. If desired, the reaction may be carried in the presence of an organic or inorganic acid.

If N,N'-bis-methoxycarbonyl-S-methyl-isothiourea and 2-amino-4-benzoyl-acetanilide are used as starting compounds, the course of the reaction in the process of the invention can be represented by the following equation:

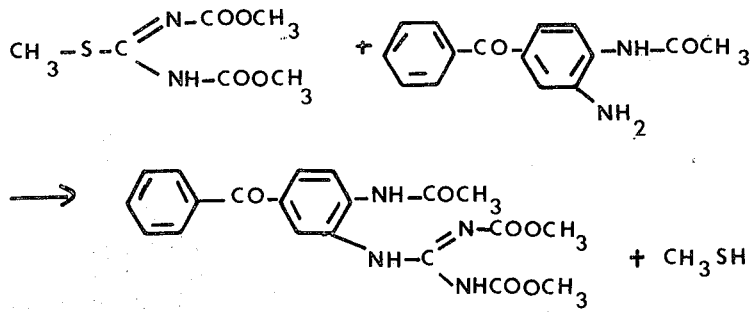

If N-methoxycarbonyl-N-propionyl-S-methyl-isothiourea and 2-amino-4-benzoyl-acetanilide are used as starting compounds, the course of the reaction in the process of the invention can be represented by the following equation:

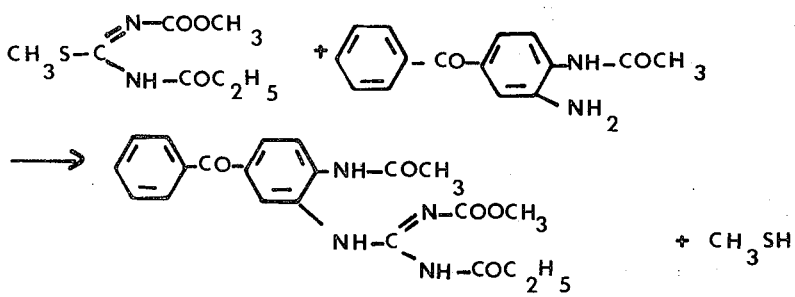

According to one embodiment of the present invention
$R^2$ is hydrogen; lower alkyl unsubstituted or substituted by phenoxy; cycloalkyl of 5 to 8 carbon atoms; benzyl; phenyl; or —NR''R''' wherein
  R'' is hydrogen or alkyl of 1 to 4 carbon atoms,
  R''' is hydrogen; lower alkyl unsubstituted or substituted by cyano or alkoxy of 1 to 4 carbon atoms; benzyl; phenyl unsubstituted or substituted by alkyl of 1 to 4 carbon atoms; and
Z is $R^3$ wherein
  $R^3$ is hydrogen; lower alkyl unsubstituted or substituted by phenoxy; alkenyl of 2 to 4 carbon atoms; alkinyl of 2 to 4 carbon atoms; cycloalkyl of 5 to 8 carbon atoms; benzyl; or phenyl unsubstituted or substituted by alkyl of 1 to 4 carbon atoms.

According to another embodiment of the present invention
$R^1$ is methyl, ethyl, isopropyl or sec.-butyl;
$R^2$ is methyl, ethyl, n-propyl, iso-propyl, n-butyl, iso-butyl, iso-amyl, cyclopentyl, cyclohexyl, benzyl, phenoxymethyl, phenyl, p-tolyl, methylamino, propylamino, butylamino, ω-cyanopentylamino, 2-methoxyethylamino, 3-ethoxypropylamino, benzylamino or phenylamino; and Z is $OR^1$, wherein $R^1$ is as above defined, or
  $R^3$ wherein $R^3$ is methyl, ethyl, n-propyl, isopropyl, n-butyl, iso-butyl, iso-amyl, cyclopentyl, cyclohexyl, propenyl, propinyl, benzyl, phenoxy-methyl or phenyl.

According to another embodiment of the present invention
$R^2$ is lower alkyl; cycloalkyl of 5 or 6 carbon atoms; benzyl; phenyl; methylphenyl; or —NR''R''' wherein
  R'' is hydrogen or alkyl of 1 to 4 carbon atoms;
  R''' is lower alkyl unsubstituted or substituted by cyano or methoxy; benzyl; or phenyl; and
Z is alkyl of 1 to 4 carbon atoms; cyclohexyl; phenyl; or phenyl substituted by methyl or methoxy.

According to another embodiment of the present invention
$R^1$ is methyl, ethyl, isopropyl or sec.-butyl;
$R^2$ is methyl, ethyl, propyl, butyl, isobutyl, pentyl, isopentyl, cyclopentyl, cyclohexyl, benzyl, phenyl, methylphenyl, phenylamino, benzylamino, β-methoxymethylamino or ω-cyanopentylamino; and
Z is methyl, ethyl, propyl, isopropyl, sec.-butyl, cyclohexyl, or phenyl unsubstituted or substituted by methyl or methoxy.

According to another embodiment of the present invention
$R^1$ is methyl or ethyl;
$R^2$ is alkyl of 1 to 4 carbon atoms, cyclohexyl or phenyl; and
Z is alkyl of 1 to 3 carbon atoms.

According to another embodiment of the present invention
$R^2$ is methyl, ethyl, n-propyl, iso-propyl, cyclohexyl or phenyl, and
Z is methyl, ethyl or iso-propyl.

R is preferably methyl or ethyl.

Formula III provides an unambiguous definition of the thioureas used as starting compounds. They are in some cases known (see Olin and Dains, J. Amer. Chem. Soc., 52, 3326 (1930) and U.S. Pat. No. 2,993,502) and can in the other cases be obtained easily analogously to the known processes. They can be prepared from known N-acylthioureas [see, for example, Berichte der deutschen Chemischen Gesellschaft, 6, 755 (1873); Ann. chim.(5), 11, 313 (1877); J. Amer. Chem.

*Soc.* 62, 3274 (1940)], by reaction, in a manner which is also known, with alkylating agents such as alkyl halides, alkyl sulphates and alkylsulphonates to give the corresponding S-alkyl-N-acylisothioureas [see, for example, *J. Org. Chem.*, 30, 560, (1965); *Chem. Pharm. Bull.* (Tokyo), 9, 245 (1961)]. These S-alkyl-N-acyl-isothioureas can then be reacted with haloformic acid esters or with pyrocarbonic acid dialkyl esters [compare *Ber. dtsch. Chem. Ges.* 71, 1797 (1938)] to give the S-alkyl-N-acyl-N'-alkoxycarbonyl-isothioureas. This last reaction corresponds to the principle of the known substitution of S-alkyl-isothioureas with chloroformic acid alkyl esters [compare *J. Amer. Chem. Soc.*, 52, 3326 (1930)].

The following isothioureas are representative of those which may be used as starting materials according to the present invention:

N,N'-bis-methoxycarbonyl-S-methyl-isothiourea (melting point 99°–100° C)
N,N'-bis-ethoxycarbonyl-S-methyl-isothiourea (melting point 50°–51° C)
N-ethoxycarbonyl-N'-propionyl-S-methyl-isothiourea (melting point 92°–94° C)
N-methoxycarbonyl-N'-propionyl-S-methyl-isothiourea (melting point 97°–99° C)
N-methoxycarbonyl-N'-ethoxyacetyl-S-methyl-isothiourea (melting point 69°–70° C)
N-methoxycarbonyl-N'-cyclohexylcarbonyl-S-methyl-isothiourea (melting point 67°–68° C)
N-methoxycarbonyl-N'-phenylacetyl-S-methyl-isothiourea (melting point 55°–56° C)
N-ethoxycarbonyl-N'-benzoyl-S-methyl-isothiourea (melting point 79°–80° C)

While the 2-amino-4-benzoyl-aniline derivatives of formula II which would be used as starting materials are per se not known, they may be easily prepared by a process analogous to that disclosed in the literature.

Thus, for example, 2-amino-4-benzoyl-acetanilide can be obtained in a two-step process from the known 2-nitro-4-benzoyl-aniline (compare, for example, *Ber. dtsch. Chem. Ges.*, 47, 2778) as follows:

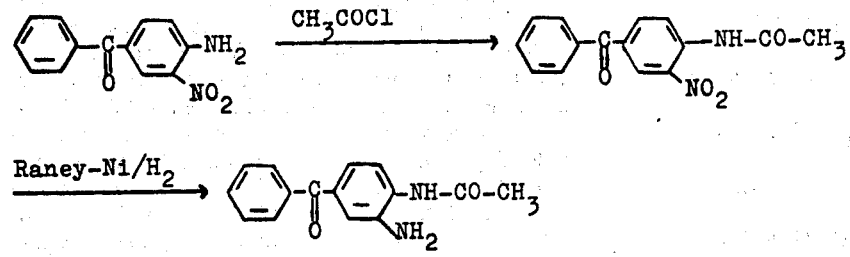

The following 2-amino-4-benzoyl-aniline derivatives are representative of those useful as starting materials according to the present invention:
2-amino-4-benzoyl-acetanilide
2-amino-4-benzoyl-propionanilide
2-amino-4-benzoyl-butyranilide
2-amino-4-benzoyl-iso-butyranilide
2-amino-4-benzoyl-valeranilide
2-amino-4-benzoyl-iso-valeranilide
2-amino-4-benzoyl-caproanilide
2-amino-4-benzoyl-iso-caproanilide
2-amino-4-benzoyl-cyclopentanecarboxylic acid anilide
2-amino-4-benzoyl-cyclohexanecarboxlic acid anilide
2-amino-4-benzoyl-phenylacetanilide
2-amino-4-benzoyl-penoxyacetanilide
2-amino-4-benzoyl-benzanilide
N-(2-amino-4-benzoyl-phenyl)-N'-methyl-urea
N-(2-amino-4-benzoyl-phenyl)-N'-ethyl-urea
N-(2-amino-4-benzoyl-phenyl)-N'-butyl-urea
N-(2-amino-4-benzoyl-phenyl)-N'-ω-cyanopentyl-urea
N-(2-amino-4-benzoyl-phenyl)-N'-β-methoxyethyl-urea
N-(2-amino-4-benzoyl-phenyl)-N'-benzyl-urea
N-(2-amino-4-benzoyl-phenyl)-N'-phenyl-urea In carrying out the process according to the invention, any polar organic solvent can be used as diluent. Preferred diluents include alcohols (such as methanol, ethanol and iso-propanol), their mixtures with water, ketones (such as acetone (anhydrous or mixed with water)) and ethers (such as dioxane and tetrahydrofurane).

The reaction can be carried out in the presence of an acid or a reaction-promoting catalyst. The acid may in principle be any organic or inorganic acid. However, the easily accessible, industrially important members of these categories are preferably employed. Hydrochloric acid, sulphuric acid, nitric acid, formic acid, acetic acid and p-toluenesulphonic acid may be mentioned as examples of such acids.

The reaction temperatures can be varied over a substantial range. In general, the reaction is carried out at between 50° C and 120° C, preferably between 60° C and 100° C. The reaction is generally carried out under normal pressure.

In carrying out the process according to the invention, 1 mol of isothiourea ether of general formula III is generally employed per 1 mol of 2-amino-4-benzoylaniline derivative of general formula II. It is possible to deviate by up to 20 percent or below this ratio without significantly reducing the yield. The reaction is preferably carried out in the boiling solvent, alkylmercaptan being produced as a by-product. On cooling the reaction mixture, the end products are obtained in a crystalline form and can be isolated by filtration and, if appropriate, purified by redissolving and reprecipitating, or recrystallizing.

The following benzoylphenylquanidines are representative of the compounds of the present invention:
N-(2-acetamido-5-benzoyl-phenyl)-N'-methoxy-carbonyl-N''-propionyl-guanidine,
N-(2-acetamido-5-benzoyl-phenyl)-N'-ethoxycarbonyl-N''-propionyl-guanidine,
N-(2-acetamido-5-benzoyl-phenyl)-N'-iso-propoxycarbonyl-N''-propionyl-guanidine,
N-(2-acetamido-5-benzoyl-phenyl)-N'-sec-butoxycarbonyl-N''-propionyl-guanidine,
N-(2-propionamido-5-benzoyl-phenyl)-N'-methoxycarbonyl-N''-propionyl-guanidine,
N-(2-butyramido-5-benzoyl-phenyl)-N'-methoxycarbonyl-N''-propionylguanidine,
N-(2-valeramido-5-benzoyl-phenyl)-N'-methoxycarbonyl-N''-propionyl-guanidine, N-(2-cyclopentanecarbonamido-5-benzoyl-phenyl)-N'-methoxycarbonyl-N''-propionyl-guanidine,
N-(2-cyclohexanecarbonamido-5-benzoyl-phenyl)-N'-methoxycarbonyl-N''-propionyl-guanidine,
N-(2-benzamido-5-benzoyl-phenyl)-N'-methoxycarbonyl-N''-propionyl-guanidine,
N-(2-acetamido-5-benzoyl-phenyl)-N'-methoxycarbonyl-N''-acetyl-guanidine,
N-(2-acetamido-5-benzoyl-phenyl)-N'-methoxycarbonyl-N''-butyryl-guanidine,
N-(2-acetamido-5-benzoyl-phenyl)-N'-methoxycarbonyl-N''-cyclohexanecarbonyl-guanidine,
N-(2-acetamido-5-benzoyl-phenyl)-N'-methoxycarbonyl-N''-benzoyl-guanidine,
N-(2-acetamido-5-benzoyl-phenyl)-N'-methoxycarbonyl-N''-phenylacetyl-guanidine,
N-(2-acetamido-5-benzoyl-phenyl)-N'-methoxycarbonyl-N''-phenoxyacetyl-guanidine,
N-[2-(2'-methylureido)-5-benzoyl-phenyl]-N'-methoxycarbonyl-N''-propionyl-guanidine,
N-[2-(2'-ethylureido)-5-benzoyl-phenyl]-N'-methoxycarbonyl-N''-propionyl-guanidine,
N-[2-(2'-butylureido)-5-benzoyl-phenyl]-N'-methoxycarbonyl-N''-propionyl-guanidine,
N-[2-(2'-ω-cyanopentylureido)-5-benzoyl-phenyl]-N'-methoxy-carbonyl-N-''-propionyl-guanidine,
N-[2-(2'-β-methoxymethylureido)-5-benzoyl-phenyl)-N'-methoxycarbonyl-N''-propionyl-guanidine,
N-[2-(2'-benzylureido)-5-benzoyl-phenyl]-N'-methoxycarbonyl-N''-propionyl-guanidine,
N-[2-(2'-phenylureido)-5-benzoyl-phenyl]-N'-methoxycarbonyl-N''-propionyl-guanidine,
N-(2-acetamido-5-benzoyl-phenyl)-N',N''-bis-methoxycarbonyl-guanidine,
N-(2-acetamido-5-benzoyl-phenyl)-N-',N''-bis-ethoxycarbonyl-guanidine,
N-(2-acetamido-5-benzoyl-phenyl)-N',N''-bis-isopropoxycarbonyl-guanidine,
N-(2-acetamido-5-benzoyl-phenyl)-N',N''-bis-sec-butoxycarbonyl-guanidine,
N-(2-propionamido-5-benzoyl-phenyl)-N',N''-bis-methoxycarbonyl-guanidine,
N-(2-butyramido-5-benzoyl-phenyl)-N',N''-bis-methoxycarbonyl-guanidine,
N-(2-iso-butyramido-5-benzoyl-phenyl)-N',N''-bis-methoxycarbonyl-guanidine,
N-(2-valeramido-5-benzoyl-phenyl)-N',N''-bis-methoxycarbonyl-guanidine,
N-(2-iso-valeramido-5-benzoyl-phenyl)-N',N''-bis-methoxycarbonyl-guanidine,
N-(2-caproamido-5-benzoyl-phenyl)-N',N''-bis-methoxycarbonyl-guanidine, N-(2-iso-caproamido-5-benzoylphenyl)-N',N''-bis-methoxycarbonyl-guanidine,
N-(2-cyclopentane-carbonamido-5-benzoyl-phenyl)-N,N''-bis-methoxycarbonyl-guanidine,
N-(2-cyclohexanecarbonamido-5-benzoyl-phenyl)-N',N''-bis-methoxycarbonyl-guanidine,
N-(2-phenylacetamido-5-benzoyl-phenyl)-N',N''-bis-methoxycarbonyl-guanidine,
N-(2-phenoxyacetamido-5-benzoyl-phenyl)-N',N''-bis-methoxycarbonyl-guanidine,
N-(2-benzamido-5-benzoyl-phenyl)-N',N''-bis-methoxycarbonyl-guanidine,
N-[2-(2'-methylureido)-5-benzoyl-phenyl]-N'-N''-bis-methoxycarbonyl-guanidine,
N-[2-(2'-ethylureido)-5-benzoyl-phenyl]-N',N''-bis-methoxycarbonyl-guanidine,
N-[2-(2'-butylureido)-5-benzoyl-phenyl]-N',N''-bis-methoxycarbonyl-guanidine,
N-[2-(2'-ω-cyanopentylureido)-5-benzoyl-phenyl]-N',N''-bis-methoxycarbonyl-guanidine,
N-[2-(2'-β-methoxyethyl-ureido)-5-benzoyl-phenyl]-N',N''-bis-methoxycarbonyl-guanidine,
N-[2-(2'-benzylureido)-5-benzoyl-phenyl]-N',N''-bis-methoxycarbonyl-guanidine, and
N-[2-(2'-phenylureido)-5-benzoyl-phenyl]-N',N''-bis-methoxycarbonyl-guanidine.

The compounds according to the invention display a surprisingly good and broad action against the following nematodes and cestodes:

1. Hookworms (for example *Uncinaria stenocephala, Ancylostoma caninum* and *Bunostomum trigonocephalum*).
2. Trichostrongylides (for example *Nippostrongylus muris, Haemonchus contortus, Trichostrongylus colubriformis* and *Cooperia curticei*).
3. Strongylides (for example *Oesophagostomum columbianum*).
4. Rhabditides (for example *Strongyloides ratti*).
5. Ascarides (for example *Ascaris suum, Toxocara canis* and *Toxascaris leonina*).
6. Pinworms (for example *Aspiculuris tetraptera*).
7. Heterakides (for example *Heterakis spumosa*).
8. Whipworms (for example *Trichuris muris*).
9. Filariae (for example *Litomosoides carinii* and *Dipetalonema witei*).
10. Cestodes (for example *Taenia spec.* and *Echinococcus spec.*).

The action was examined in animal experiments after oral and parenteral administration to test animals heavily infected with parasites. The dosages used were tolerated very well by the test animals. These experiments are described in detail below.

The present invention also includes anthelmintic compositions which comprise anthelmintically effective amounts of a benzoylphenylguanidine according to the present invention.

The pharmaceutical compositions of the present invention contain a major or minor amount, e.g., 0.1% to 99.5%, preferably 0.5% to 95% of active ingredient as above defined in combination with a pharmaceutically acceptable, nontoxic, inert diluent or carrier, the carrier comprising one or more solid, semi-solid or liquid diluent, diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the dosage will be from 1 to 100 mg/kg of body weight per day. In some instances a sufficient therapeutic effect can be obtained at a lower dose, while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is a 50 mg to 10 g of active ingredient.

While the routes of administration include oral, parenteral (i.e., intramuscular, intraperitoneal, and intravenous), rectal, and topical, oral administration is particularly preferred.

The preferred pharmaceutical compositions and medicaments are therefore those adapted for oral administration, such as tablets and capsules.

The anthelmintic activity of the compounds of the present invention is more particularly illustrated by the following examples:

EXAMPLE A

Hookworm test/sheep and dogs

Sheep experimentally infected with *Bunostomum trigonocephalum* were treated after the end of the pre-patency time of the parasites. The stated amount of active compound was administered orally as pure active compound in gelatine capsules.

Dogs experimentally infected with *Uncinaria stenocephala* or *Ancylostoma caninum* were treated after the end of the pre-patency time of the parasites. The stated amount of active compound was administered orally as pure active compound in gelatine capsules.

The degree of effectiveness is determined by counting the worms expelled after the treatment and the worms surviving in the test animals after dissection and calculating the percentage of worms expelled.

The active compounds tested, the dosages used and the effect can be seen from the table which follows.

This table lists the active compounds and the minimum dosage in mg of active compound per kg of body weight of the test animal which reduces the worm infection of the test animal by more than 90%.

pound was administered orally as an aqueous suspension.

The effectiveness of the preparation is determined by counting, after dissection, the worms which have remained in the test animal, in comparison to untreated control animals, and calculating the percentage effect therefrom.

The table which follows lists the active compounds and the minimum dosage which reduces the worm infection of the test animals by more than 90%, in comparison to related known compounds.

Table 1
(accompanying Example A)

| Active compound according to the invention | Minimum effective dose (red. >90%) in mg/kg |
|---|---|
| Ph-CO-C6H3(CH3)-NH-CO-CH3; NHC(=N-COOCH3)-NHCOC2H5 | Bunostomum trig. 25; Uncinaria sten. 3 × 25; Ancylostoma can. 3 × 25 |
| Ph-CO-C6H3-NH-CO-C3H7 n; NH-C(=N-CO-OCH3)-NH-COOCH3 | Bunostomum trig. 5 |
| Ph-CO-C6H3-NH-CO-C3H7 n; NH-C(-NH-COC2H5)=N-COOCH | Bunostomum trig. 5; Ancylostoma can. 3 × 10; Uncinaria sten. 3 × 5 |
| Ph-CO-C6H3-NH-CO-CH2-CH3; NH-C(=N-COOCH3)-NH-COOCH3 | Bunostomum trig. 5. |

EXAMPLE B

*Nippostrongylus muris* — rats

Rats experimentally infected with *Nippostrongylus muris* were treated after the end of the pre-patency time of the parasites. The stated amount of active com-

Table 2
(accompanying Example B)

| Active compound according to the invention | Minimum effective dose (red. >90%) in mg/kg |
|---|---|
| 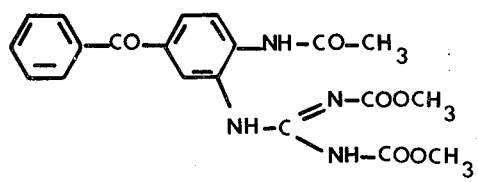 | 50 |

Table 2-continued
(accompanying Example B)
| Active compound according to the invention | Minimum effective dose (red. >90%) in mg/kg |
|---|---|
| 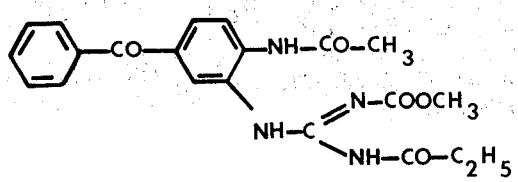 | 50 |
| 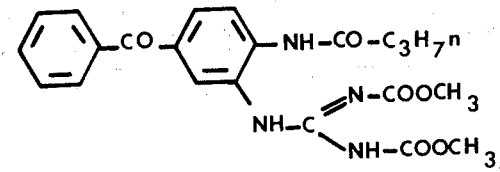 | 250 |
| 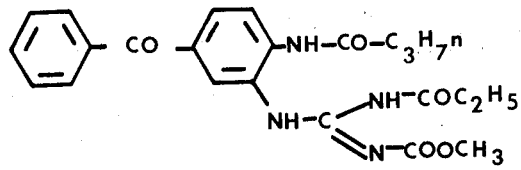 | 50 |
| 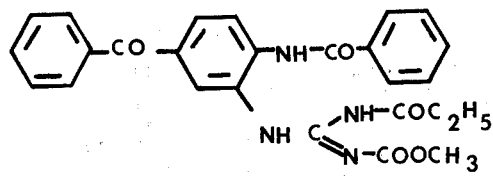 | 250 |
| 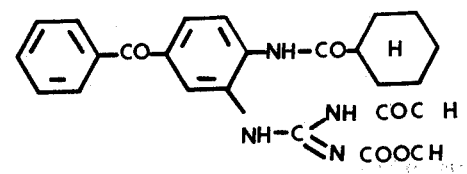 | 250 |
| 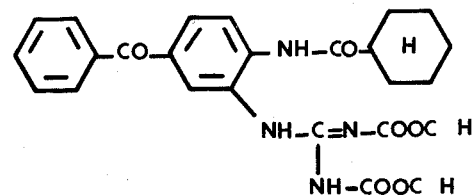 | 250 |
| Related compounds, for comparison (known from DOS (German Published Specification) 2,117,293) | |
| 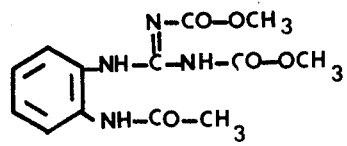 | >500 |
| 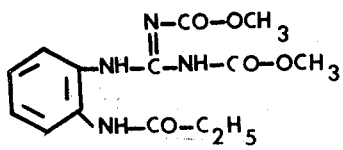 | 500 |

EXAMPLE C

Gastric and intestinal worm test/sheep

Sheep experimentally infected with *Haemonchus contortus*, *Cooperia curticei* or *Trichostrongylus colubriformis* were treated after the end of the pre-patency time of the parasites. The stated amount of active compound was administered orally as pure active compound in gelatine capsules.

The effectiveness is determined by quantitatively counting the worm eggs excreted with the faeces, before and after treatment.

Complete cessation of the excretion of eggs after the treatment means that the worms have been expelled or are so heavily damaged that they can no longer produce any eggs (effective dose).

The active compounds tested and the effective dosages (minimum effective dose) can be seen from the following table.

Table 3

(accompanying Example C)

| Active compound according to the invention | Parasite | Minimum effective dose (red. >90%) in mg/kg |
|---|---|---|
| 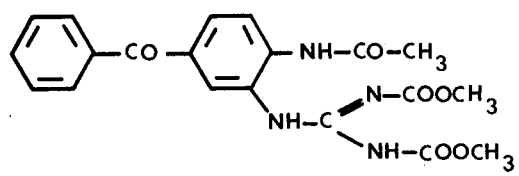 | *Haemonchus contortus* *Trichostrongylus colubriformis* *Cooperia curticei* | 25 10 10 |
| 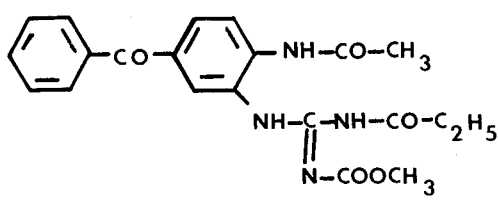 | *Haemonchus contortus* *Trichostrongylus colubriformis* *Cooperia curticei* | 10 5 10 |
| 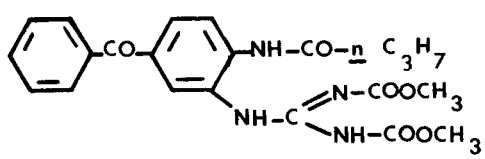 | *Haemonchus contortus* *Trichostrongylus colubriformis* | 5 5 |
| 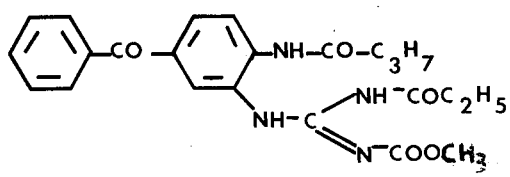 | *Haemonchus contortus* *Trichostrongylus colubriformis* | 5 2.5 |
| 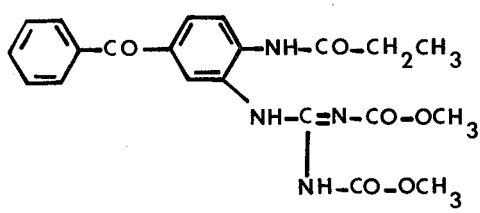 | *Haemonchus contortus* *Trichostrongylus colubriformis* | 5 2.5 |

Table 3-continued
(accompanying Example C)

| Active compound according to the invention | Parasite | Minimum effective dose (red. >90%) in mg/kg |
|---|---|---|
| 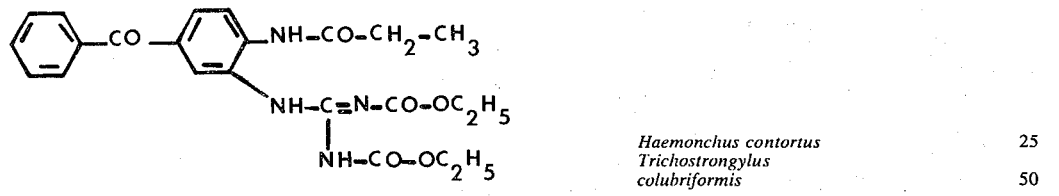 | Haemonchus contortus | 25 |
| | Trichostrongylus colubriformis | 50 |
| 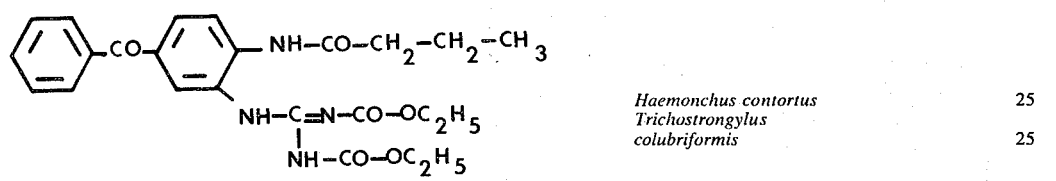 | Haemonchus contortus | 25 |
| | Trichostrongylus colubriformis | 25 |
| Related compounds, for comparison (known from DOS (German Published Specification) 2,117,293) | | |
| ![structure] NH–C(=N–CO–OCH₃)–NH–CO–OCH₃ on benzene with NH–CO–CH₃ | Haemonchus contortus | >100 |
| | Trichostrongylus colubriformis | 50 |
| ![structure] NH–C(=N–CO–OCH₃)–NH–CO–OCH₃ on benzene with NH–CO–C₂H₅ | Haemonchus contortus | 50 |
| | Trichostrongylus colubriformis | 10 |

EXAMPLE D

Nodule worm test/sheep

Sheep experimentally infected with *Oesophagostomum columbianum* were treated after the end of the pre-patency time of the parasites.

The stated amount of active compound was administered orally as pure active compound in gelatine capsules.

The degree of effectiveness is determined by counting the worms expelled after the treatment and the worms surviving in the test animals after dissection and calculating the percentage of worms expelled.

The active compound tested and the effective dose (minimum effective dose) can be seen from the table which follows.

Table 4
(accompanying Example D)

| Active compound according to the invention | Minimum effective dose (red. >90%) in mg/kg |
|---|---|
| 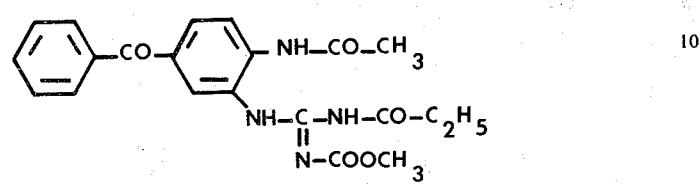 | 10 |

Table 4-continued
(accompanying Example D)

| Active compound according to the invention | Minimum effective dose (red. >90%) in mg/kg |
|---|---|
| Ph-CO-C6H3(NH-CO-C3H7-n)(NH-C(=N-COOCH3)(NH-COOCH3)) | 5 |
| Ph-CO-C6H3(NH-CO-C3H7-n)(NH-C(NH-COC2H5)(=N-COOCH3)) | 5 |
| Ph-CO-C6H3(NH-CO-CH2CH3)(NH-C(=N-CO-OCH3)(NH-CO-OCH3)) | 5 |

EXAMPLE E

*Strongyloides ratti*/rats

Rats experimentally infected with *Strongyloides ratti* were treated after the end of the pre-patency time of the parasites. The stated amount of active compound was administered orally as an aqueous suspension.

The effectiveness of the preparation is determined by counting, after dissection, the worms which have remained in the test animal, in comparison to untreated control animals, and calculating the percentage effect therefrom.

The table which reduces the worm infection of the test animals by more than 90%, in comparison to related known compounds.

Table 5
(accompanying Example E)

| Active compound according to the invention | Minimum effective dose (red. >90%) in mg/kg |
|---|---|
| Ph-CO-C6H3(NH-CO-CH3)(NH-C(=N-COOCH3)(NH-COOCH3)) | 50 |
| Ph-CO-C6H3(NH-CO-CH3)(NH-C(=N-COOCH3)(NH-CO-C2H5)) | 25 |
| Ph-CO-C6H3(NH-CO-CH3)(NH-C(NH-CO-Ph)(=N-COOC2H5)) | 250 |
| Ph-CO-C6H3(NH-CO-C3H7-n)(NH-C(=N-COOCH3)(NH-COOCH3)) | 10 |

Table 5-continued (accompanying Example E)

| Active compound according to the invention | Minimum effective dose (red. >90%) in mg/kg |
|---|---|
| Structure: phenyl-CO-C₆H₃(NH-CO-C₃H₇n)(NH-C(NH-COC₂H₅)=N-COOCH₃) | 2.5 |
| Structure: phenyl-CO-C₆H₃(NH-CO-phenyl)(NH-C(NH-COC₂H₅)=N-COOCH₃) | 250 |
| Structure: phenyl-CO-C₆H₃(NH-CO-cyclohexyl)(NH-C(NH-CO·C₂H₅)=N-COOCH₃) | 250 |
| Structure: phenyl-CO-C₆H₃(NH-CO-cyclohexyl)(NH-C(=N-COOC₂H₅)(NH-COOC₂H₅)) | 250 |
| Structure: phenyl-CO-C₆H₃(NH-CO-CH₂CH₃)(NH-C(=N-CO-OCH₃)(NH-CO-OCH₃)) | 50 |

Related compounds for comparison (known from DOS (German Published Specification) 2,117,293):

| | |
|---|---|
| Structure: C₆H₄(NH-C(=N-CO-OCH₃)-NH-CO-OCH₃)(NH-CO-C₂H₅) | 250 |
| Structure: C₆H₄(NH-C(=N-CO-OCH₃)-NH-CO-OCH₃)(NH-CO-CH₃) | 100 |

EXAMPLE F

Ascarides test/dogs and rats

The amount of active compound used was administered orally, as pure active compound in gelatine capsules, to dogs naturally or experimentally infected with *Toxascaris leonina* or *Toxocara canis*.

Rats experimentally infected with *Ascaris suum* were treated 2 to 4 days after infection. The stated amount of active compound was administered orally as an aqueous suspension.

The effectiveness of the preparation is determined by counting, after dissection, the worms which have remained in the test animal, in comparison to untreated control animals, and calculating the percentage effect therefrom.

The table which follows lists the active compounds and the minimum dosage which reduces the worm infestation of the test animals by more than 90%, in comparison to related known compounds.

Table 6
(accompanying Example F)

| Active compound according to the invention | Parasite | Minimum effective dose (red. >90%) in mg/kg |
|---|---|---|
| [structure: Ph-CO-C6H3(NH-CO-CH3)(NH-C(=N-COOCH3)(NH-COOCH3))] | Ascaris suum | 10 |
| [structure: Ph-CO-C6H3(NH-CO-CH3)(NH-C(=N-COOCH3)(NH-CO-C2H5))] | Ascaris suum<br>Toxascaris leonina<br>Toxocara canis | 25<br>25<br>25 |
| [structure: Ph-CO-C6H3(NH-CO-C3H7n)(NH-C(NH-CO-C2H5)(=N-CO-OCH3))] | Toxascaris leonina<br>Toxocara canis | 3 × 1<br>3 × 1 |

| Active compound according to the invention | Minimum effective dose (red. >90%) in mg/kg | Ascaris suum |
|---|---|---|
| [structure: Ph-CO-C6H3(NH-CO-CH3)(NH-C(NH-CO-Ph)(=N-COOC2H5))] | 250 | " |
| [structure: Ph-CO-C6H3(NH-CO-C3H7n)(NH-C(=N-COOCH3)(NH-CCOCH3))] | 10 | " |
| [structure: Ph-CO-C6H3(NH-CO-Ph)(NH-C(NH-COC2H5)(=N-COOCH3))] | 250 | " |
| [structure: Ph-CO-C6H3(NH-CO-C6H11)(NH-C(NH-CO·C2H5)(=N-COOCH3))] | 250 | " |

Table 6-continued (accompanying Example F)

| Active compound according to the invention | Parasite | Minimum effective dose (red. >90%) in mg/kg |
|---|---|---|
| ![structure: Ph-CO-C6H3(NH-CO-C6H11)(NH-C(=N-COOC2H5)-NH-COOC2H5)] | 250 | " |
| ![structure: Ph-CO-C6H3(NH-CO-CH2CH3)(NH-C(=N-CO-OCH3)-NH-CO-OCH3)] | 50 | " |

Related compounds, for comparison (known from DOS (German Published Specification) 2,117,293)

| | | |
|---|---|---|
| ![structure: C6H4(NH-C(=N-CO-OCH3)-NH-CO-OCH3)(NH-CO-CH3)] | Ascaris suum Inactive | |
| ![structure: C6H4(NH-C(=N-CO-OCH3)-NH-CO-OCH3)(NH-CO-C2H5)] | Ascaris suum Inactive | |

EXAMPLE G

Heterakis spumosa/mice

Mice experimentally infected with *Heterakis spumosa* were treated after the end of the pre-patency time of the parasites.

The stated amount of active compound was administered orally as an aqueous suspension.

The effectiveness of the compound is determined by counting, after dissection, the worms which have remained in the test animal, in comparison to untreated control animals, and calculating the percentage effect therefrom.

Table 7

(accompanying Example G)

| Active compound according to the invention | Minimum effective dose (red. >90%) in mg/kg |
|---|---|
| ![structure: Ph-CO-C6H3(NH-CO-CH3)(NH-C(=N-COOCH3)-NH-COOCH3)] | 50 |

Table 7-continued
(accompanying Example G)
| Active compound according to the invention | Minimum effective dose (red. >90%) in mg/kg |
|---|---|
| 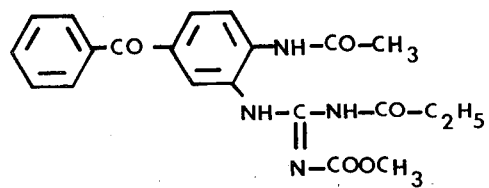 | 10 |
| 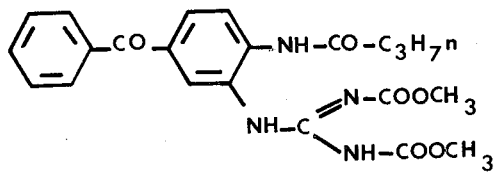 | 250 |
| 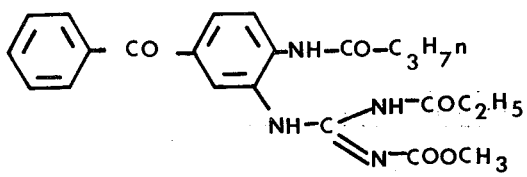 | 10 |
| 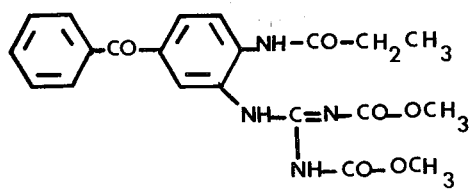 | 50 |
| 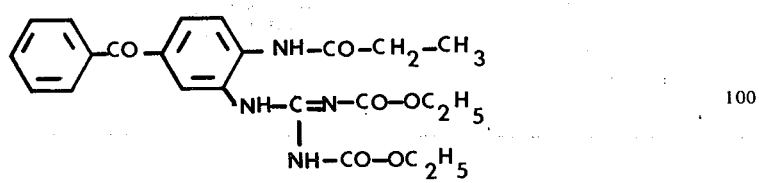 | 100 |
| 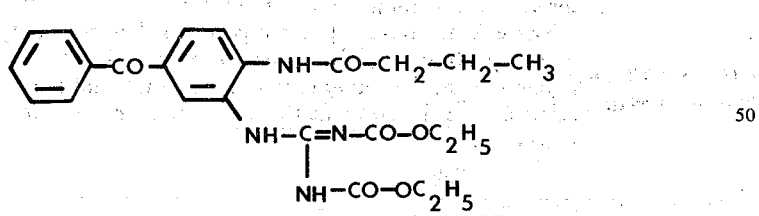 | 50 |
Known compound for comparison (known from DOS (German Published Specification) 2,117,293)
| | |
|---|---|
| 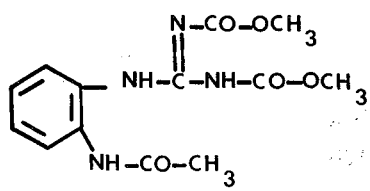 | Inactive |

EXAMPLE H

*Aspiculuris tetraptera*/mice

Mice experimentally infected with *Aspiculuris tetraptera* were treated after the end of the pre-patency time of the parasites.

The stated amount of active compound was administered orally as an aqueous suspension.

The effectiveness of the compound is determined by counting, after dissection, the worms which have remained in the test animal, in comparison to untreated control animals, and calculating the percentage effect therefrom.

Table 8
(accompanying Example H)

| Active compound according to the invention | Minimum effective dose (red. >90%) in mg/kg |
| --- | --- |
| Ph-CO-C6H3(NH-CO-CH3)(NH-C(=N-COOCH3)(NH-COOCH3)) | 25 |
| Ph-CO-C6H3(NH-CO-CH3)(NH-C(=N-COOCH3)(NH-CO-C2H5)) | 10 |
| Ph-CO-C6H3(NH-CO-C3H7-n)(NH-C(=N-COOCH3)(NH-COOCH3)) | 250 |
| Ph-CO-C6H3(NH-CO-C3H7-n)(NH-C(=N-COOCH3)(NH-COC2H5)) | 25 |
| Ph-CO-C6H3(NH-CO-CH2CH3)(NH-C(=N-CO-OCH3)(NH-CO-OCH3)) | 10 |
| Ph-CO-C6H3(NH-CO-CH2-CH3)(NH-C(=N-CO-OC2H5)(NH-CO-OC2H5)) | 50 |
| Ph-CO-C6H3(NH-CO-CH2-CH2-CH3)(NH-C(=N-CO-OC2H5)(NH-CO-OC2H5)) | 50 |

Table 8-continued

Known compound for comparison (known from DOS (German Published Specification) 2,117,293)

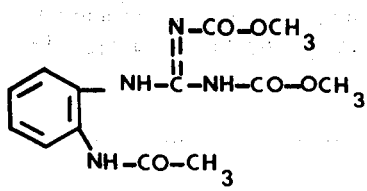

Inactive

Table I

*Trichuris muris*/mice

Mice experimentally infected with *Trichuris muris* were treated after the end of the pre-patency time of the parasites.

The stated amount of active compound was administered orally as an aqueous suspension.

The effectiveness of the preparation is determined by counting, after dissection, the worms which have remained in the test animal, in comparison to untreated control animals, and calculating the percentage effect therefrom.

Table 9
(accompanying Example I)

| Active compound according to the invention | Minimum effective dose (red. >90%) in mg/kg |
|---|---|
| [structure] | 50 |
| [structure] | 10 |
| [structure] | 25 |
| [structure] | 10 |
| [structure] | 500 |

Table 9-continued (accompanying Example I)

| Active compound according to the invention | Minimum effective dose (red. >90%) in mg/kg |
|---|---|
| 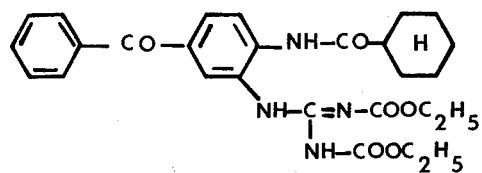 | 250 |
| 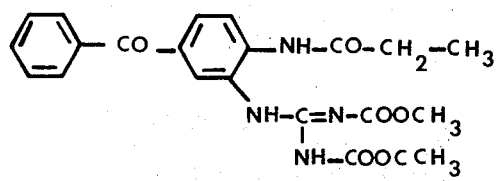 | 25 |
| 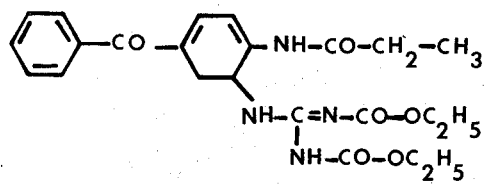 | 100 |
| 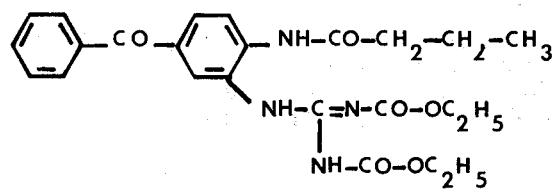 | 25 |

The following nonlimitative examples more particularly illustrate the present invention:

EXAMPLE 1

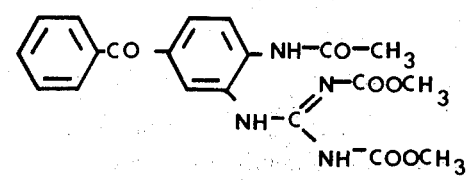

51 g (0.2 mol) of 2-amino-4-benzoyl-acetanilide of melting point 136°C, 41.2 g (0.2 mol) of N,N'-bis-methoxycarbonyl-isothiourea S-methyl ether and 2.6 g (0.015 mol) of p-toluenesulphonic acid in 600 ml of methanol are boiled for 2.5 hours while stirring, under reflux. N-(2-Acetamido-5-benzoyl-phenyl)-N'-N''-bis-methoxycarbonyl-guanidine hereupon precipitates. It is filtered off hot, well rinsed with methanol and dried in vacuo; melting point 185°C, yield 65 g.

The following compounds according to the present invention are produced by a process analogous to that described above from the reactants set forth below:

The following were produced by analogous processes:

From 2-amino-4-benzoyl-n-butyranilide of melting point 142°C and N,N′-bis-methoxycarbonyl-S-methyl-isothiourea:

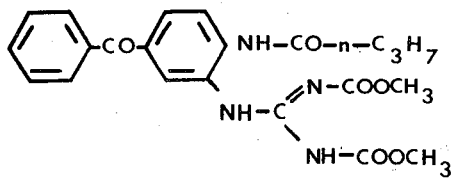

of melting point 155°C;

From 2-amino-4-benzoyl-n-butyranilide of melting point 142°C and N,N′-bis-ethoxycarbonyl-S-methyl-isothiourea:

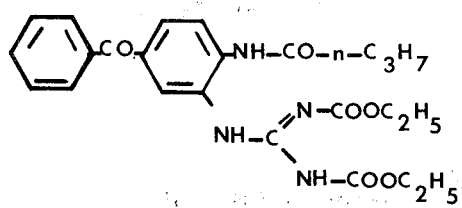

of melting point 153°C

From 2-amino-4-benzoyl-cyclohexanecarboxylic acid anilide of melting point 185°C and N,N′-bis-ethoxycarbonyl-S-methyl-isothiourea:

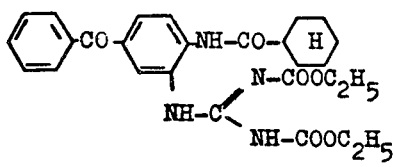

of melting point 160°C;

(N-(2-butyrylamino)-5-benzoylphenyl)-N′-N″-bis-ethoxycarbonylguanidine);

From 2-amino-4-benzoyl-propionylanilide of melting point 144°C and N-N′-bis-methoxycarbonyl-S-methyl-isothiourea:

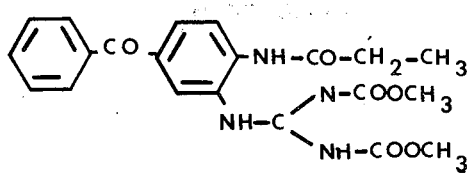

of melting point 182°C

From 2-amino-4-benzoyl-benzanilide of melting point 196°C and N,N′-bis-methoxycarbonyl-S-methyl-isothiourea:

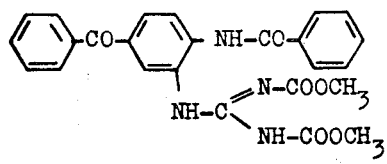

of melting point 212°C.

(N-(2-propionylamino-5-benzoylphenyl)-N′-N″-bis-methoxycarbonyl-guanidine);

From 2-amino-4-benzoyl-propionylanilide and N-N′-bis-ethoxycarbonyl-S-methyl-isothiourea:

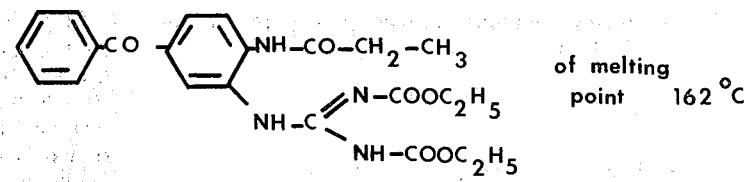

of melting point 162°C (N-(2-propionylamino-5-benzoylphenyl)-N′-N″-bis-ethoxycarbonylguanidine);

From 2-amino-4-benzoyl-acetanilide and N,N′-bis-isopropoxycarbonyl-S-methyl-isothiourea:

EXAMPLE 2

The following compounds according to the present invention are produced by a process analogous to that described above from the reactants set forth below:

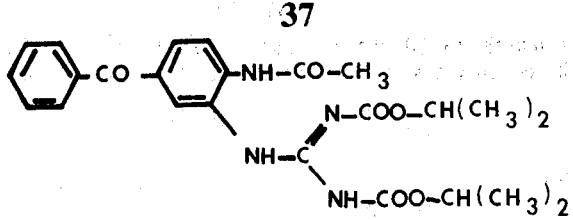

of melting point 162°C;

From 2-amino-4-benzoyl-propionylanilide and N,N'-bis-isopropoxycarbonyl-S-methyl-isothiourea:

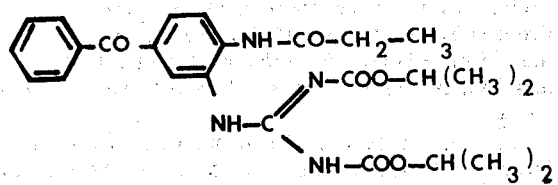

of melting point 157°C;

From 2-amino-4-benzoyl-n-butyranilide and N,N'-bis-isopropoxycarbonyl-S-methyl-isothiourea:

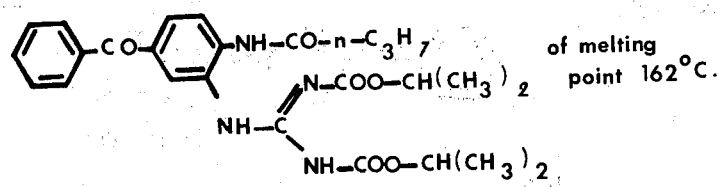

of melting point 162°C.

EXAMPLE 3

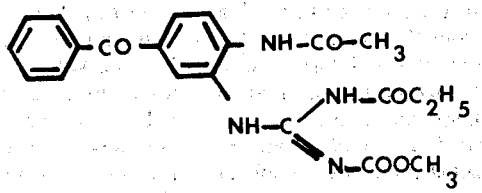

51 g (0.2 mol) of 2-amino-4-benzoyl-acetanilide of melting point 136°C, 44 g (0.2 mol) of N-methoxycarbonyl-N'-propionyl-isothiourea S-methyl ether and 2.6 g (0.015 mol) of p-toluenesulphonic acid in 500 ml of methanol are boiled for 2 hours under reflux, while stirring. On cooling the solution, which has been filtered hot in an ice bath, N-(2-acetamido-5-benzoyl-phenyl)-N'-methoxycarbonyl-N''-propionyl-guanidine crystallizes out. It is filtered off, rinsed with ether and dried in vacuo; melting point 167°C, yield 43 g.

The following compounds according to the present invention are produced by a process analogous to that described above from the reactants set forth below:

From 2-amino-4-benzoyl-acetanilide and N-ethoxycarbonyl-N'-benzoyl-S-methyl-isothiourea:

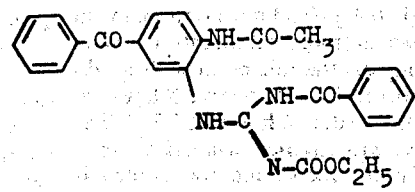

of melting point 173°C;

From 2-amino-4-benzoyl-n-butyranilide and N-methoxycarbonyl-N'-propionyl-S-methyl-isothiourea:

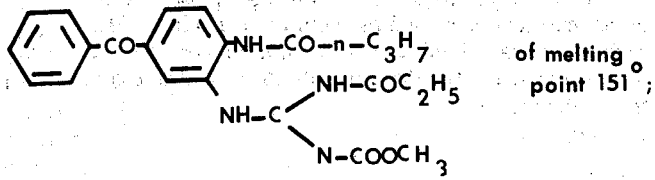

of melting point 151°;

From 2-amino-4-benzoyl-cyclohexanecarboxylic acid anilide and N-methoxycarbonyl-N'-propionyl-S-methyl-isothiourea:

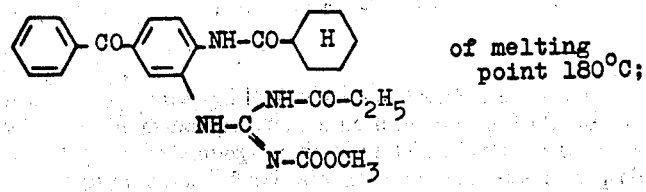

of melting point 180°C;

From 2-amino-4-benzoyl-benzanilide and N-methoxycarbonyl-N'-propionyl-S-methyl-isothiourea:

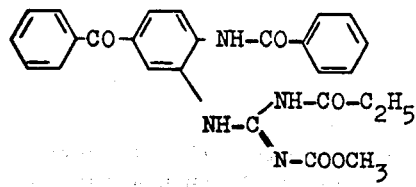

The following represents the preparation of a representative 2-amino-4-benzoyl-acetanilide starting material:

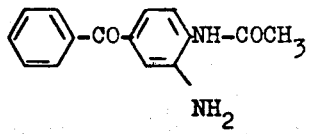

2-Amino-4-benzoyl-acetanilide can be obtained in a two-stage process from the known 2-nitro-4-benzoyl-aniline, as follows:
1st step

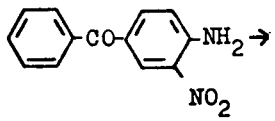

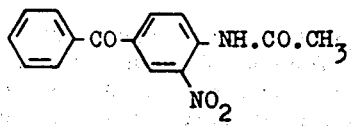

A solution of 26.1 g (0.33 mol) of acetyl chloride in 50 ml of dry benzene is added dropwise to a solution of 80.7 g (0.33 mol) of 2-nitro-4-benzoyl-aniline, known from the literature, and 26.4 g (0.33 mol) of pyridine in 800 ml of dry benzene at room temperature, while stirring. After the slightly exothermic reaction has subsided, the mixture is stirred for a further 1.5 hours at room temperature and a further 2 hours at 75°C. The water-soluble pyridine hydrochloride which has separated out is then filtered off hot, and the 2-nitro-4-benzoyl-acetanilide which crystallizes out on cooling the filtrate is well stirred with dilute hydrochloric acid, filtered off, dried and purifed by recrystallization from ethanol; melting point 145°C, yield 70 g. The yield can be increased yet further by working up the mother liquor extraction by shaking with dilute aqueous HCl, separation and drying of the organic phase, evaporation of the solvent and recrystallization of the residue from ethanol.
2nd step

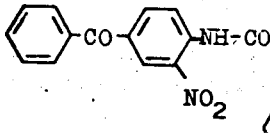

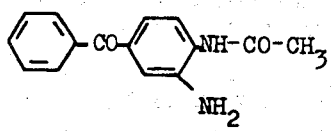

65 g of 2-nitro-4-benzoyl-acetanilide of melting point 145°C in 500 ml of tetrahydrofuran are hydrogenated with 5 g of Raney nickel at 50 atmospheres gauge hydrogen pressure, for a reaction time of 3 hours. In the course thereof the temperature rises from 20 to 35°C; the consumption of $H_2$ corresponds to the calculated of melting point 182°C;

amount. After cooling, the catalyst is filtered off, the solvent is evaporated and the oily residue is recrystallized from ethanol. Hereupon, 2-amino-4-benzoyl-acetanilide of melting point 136°C is obtained in a yield of 38 g.

The remaining 2-amino-4-benzoyl-aniline derivatives of formula II used as starting materials in the present invention may be prepared in a manner analogous to that described above.

What is claimed is:
1. A benzoylphenylguanidine of the formula

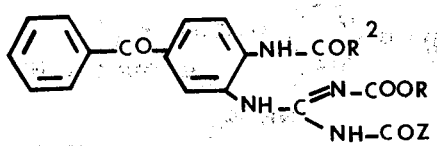

wherein
$R^1$ is alkyl of 1 to 4 carbon atoms;
$R^2$ is hydrogen; alkyl of 1 to 18 carbon atoms unsubstituted or substituted by a substituent selected from the group consisting of halogen, cyano, alkoxy of 1 to 4 carbon atoms, alkoxycarbonyl of 2 to 5 carbon atoms, phenoxy, halophenoxy, lower alkylphenoxy and lower alkoxyphenoxy; cycloalkyl of 5 to 8 carbon atoms; benzyl unsubstituted or substituted by a substituent selected from the group consisting of halogen, alkyl of 1 to 4 carbon atoms and alkoxy of 1 to 4 carbon atoms; or phenyl unsubstituted or substituted by a substituent selected from the group consisting of halogen, alkyl of 1 to 4 carbon atoms and alkoxy of 1 to 4 carbon atoms; and is hydrogen; alkyl of 1 to 18 carbon atoms unsubstituted or substituted by a substituent selected from the group consisting of halogen, cyano, alkoxy of 1 to 4 carbon atoms, alkoxycarbonyl of 2 to 5 carbon atoms, phenoxy, halophenoxy, lower alkylphenoxy and lower alkoxyphenoxy; alkenyl of 2 to 12 carbon atoms; alkinyl of 2 to 12 carbon atoms; cycloalkyl of 5 to 8 carbon atoms; benzyl unsubstituted or substituted by a substituent selected from the group consisting of halogen, alkyl of 1 to 4 carbon atoms and alkoxy of 1 to 4 carbon atoms; or phenyl unsubstituted or substituted by a substituent selected from the group consisting of halogen, alkyl of 1 to 4 carbon atoms and alkoxy of 1 to 4 carbon atoms.

2. A compound according to claim 1 wherein
$R^2$ is hydrogen; lower alkyl unsubstituted or substituted by phenoxy; cycloalkyl of 5 to 8 carbon atoms; benzyl; or phenyl; and
Z is hydrogen; lower alkyl unsubstituted or substituted by phenoxy; alkenyl of 2 to 4 carbon atoms; alkinyl of 2 to 4 carbon atoms; cycloalkyl of 5 to 8 carbon atoms; benzyl; or phenyl unsubstituted or substituted by alkyl of 1 to 4 carbon atoms.

3. A compound according to claim 1 wherein
$R^1$ is methyl, ethyl, isopropyl or sec.-butyl;

R² is methyl, ethyl, n-propyl, iso-propyl, n-butyl, iso-butyl, iso-amyl, cyclopentyl, cyclohexyl, benzyl, phenoxymethyl, phenyl, p-tolyl, methylamino, propylamino, butylamino ω-cyanopentylamino, 2-methoxyethylamino, 3-ethoxypropylamino, benzylamino or phenylamino; and Z is methyl, ethyl, n-propyl, isopropyl, n-butyl, iso-butyl, iso-amyl, cyclopentyl, cyclohexyl, propenyl, propinyl, benzyl, phenoxymethyl or phenyl.

4. A compound according to claim 1 wherein
R² is lower alkyl; cycloalkyl of 5 or 6 carbon atoms; benzyl; phenyl; or methylphenyl; and
Z is alkyl of 1 to 4 carbon atoms; cyclohexyl; phenyl; or phenyl substituted by methyl or methoxy.

5. A compound according to claim 1 wherein R¹ is methyl, ethyl, isopropyl or sec.-butyl;
R² is methyl, ethyl, propyl, butyl, isobutyl, pentyl, isopentyl, cyclopentyl, cyclohexyl, benzyl, phenyl, methylphenyl, phenylamino, benzylamino, β-methoxymethylamino or ω-cyanopentylamino; and
Z is methyl, ethyl, propyl, isopropyl, sec.-butyl, cyclohexyl, or phenyl unsubstituted or substituted by methyl or methoxy.

6. A compound according to claim 1 wherein
R¹ is methyl or ethyl;
R² is alkyl of 1 to 4 carbon atoms; cyclohexyl or phenyl; and
Z is alkyl of 1 to 3 carbon atoms.

7. A compound according to claim 6 wherein
R² is methyl, ethyl, n-propyl, iso-propyl, cyclohexyl or phenyl, and
Z is methyl, ethyl or iso-propyl.

8. The compound according to claim 1 which is

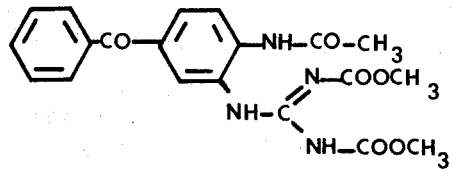

9. The compound according to claim 1 which is

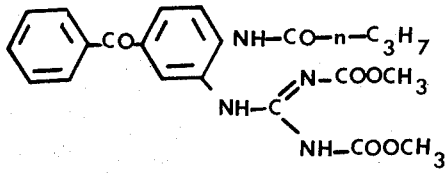

10. The compound according to claim 1 which is

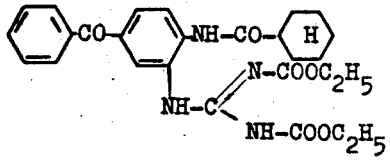

11. The compound according to claim 1 which is

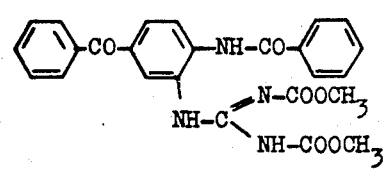

12. The compound according to claim 1 which is

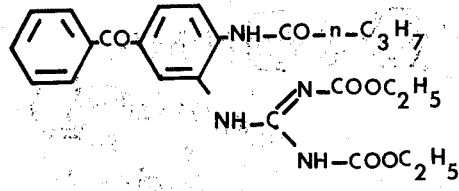

13. The compound according to claim 1 which is

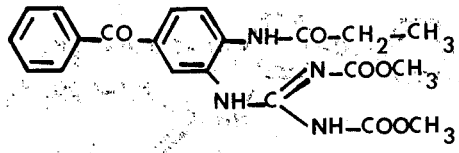

14. The compound according to claim 1 which is

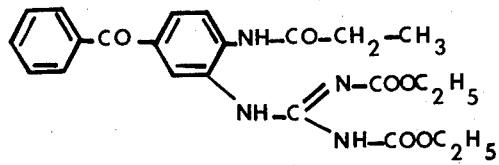

15. The compound according to claim 1 which is

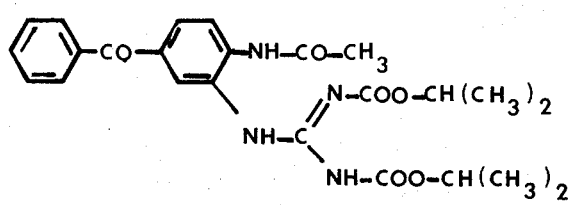

16. The compound according to claim 1 which is

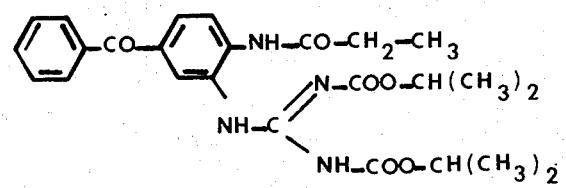

17. The compound according to claim 1 which is

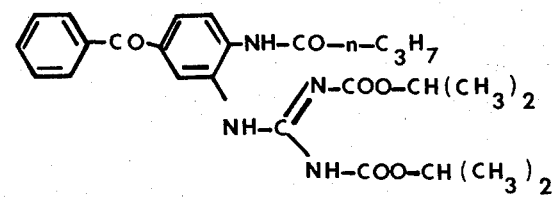

18. The compound according to claim 1 which is

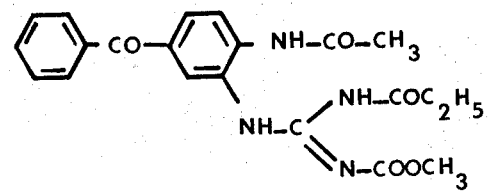

19. The compound according to claim 1 which is
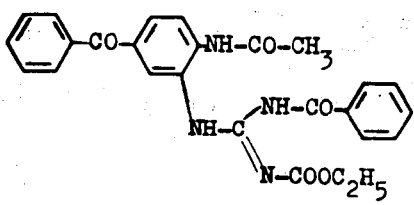
20. The compound according to claim 1 which is
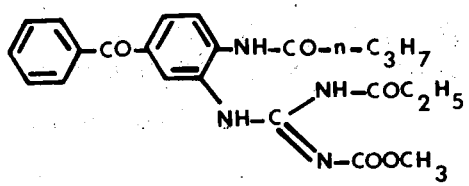
21. The compound according to claim 1 which is
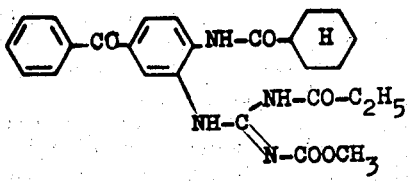
22. The compound according to claim 1 which is
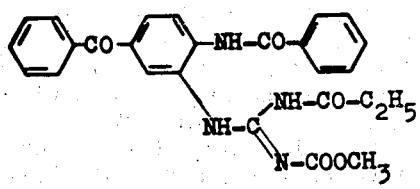
* * * * *

UNITED STATES PATENT AND TRADEMARK OFFICE
CERTIFICATE OF CORRECTION

PATENT NO. : 3,950,395
DATED : April 13, 1976
INVENTOR(S) : HEINRICH KOLLING ET AL It is certified that error appears in the above-identified patent and that said Letters Patent are hereby corrected as shown below:

Columns 11 and 12, Table 1, the third structural formula should read:

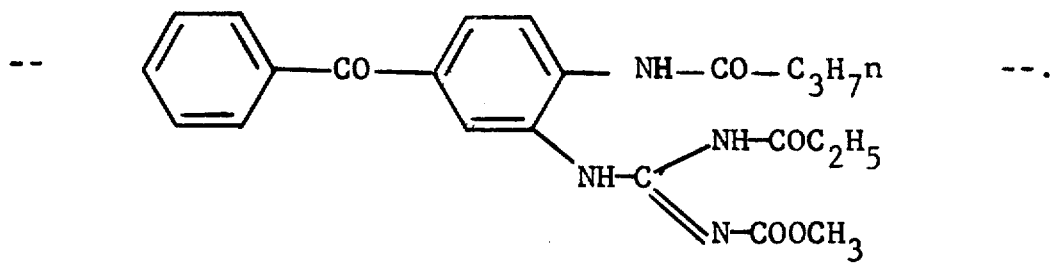

Columns 13 and 14, Table 2, fifth structural formula should read:

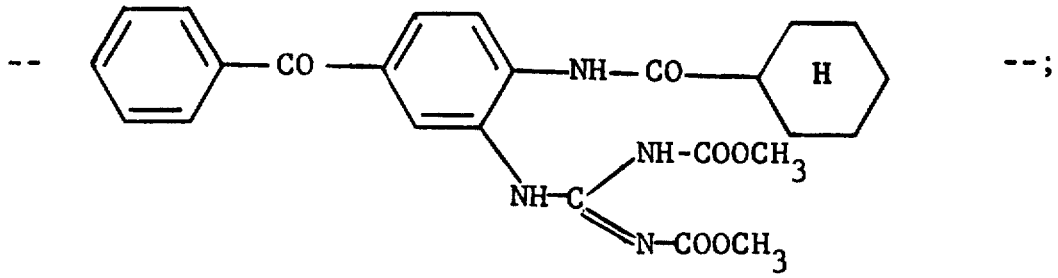

UNITED STATES PATENT AND TRADEMARK OFFICE
CERTIFICATE OF CORRECTION

PATENT NO. : 3,950,395
DATED : April 13, 1976
INVENTOR(S) : HEINRICH KOLLING ET AL It is certified that error appears in the above-identified patent and that said Letters Patent are hereby corrected as shown below:

same columns, sixth structural formula should read:

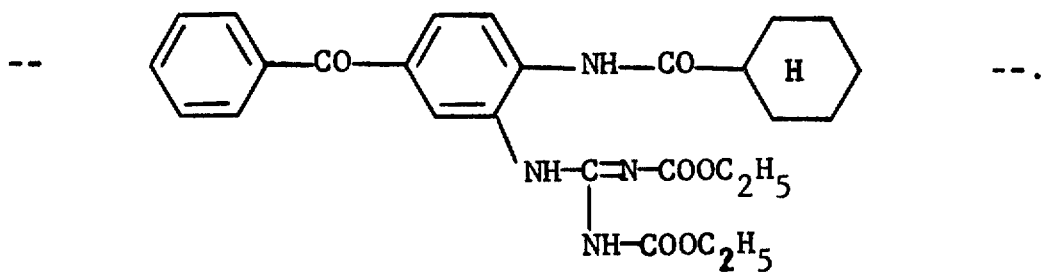

Columns 23 and 24, third structural formula from the bottom should read:

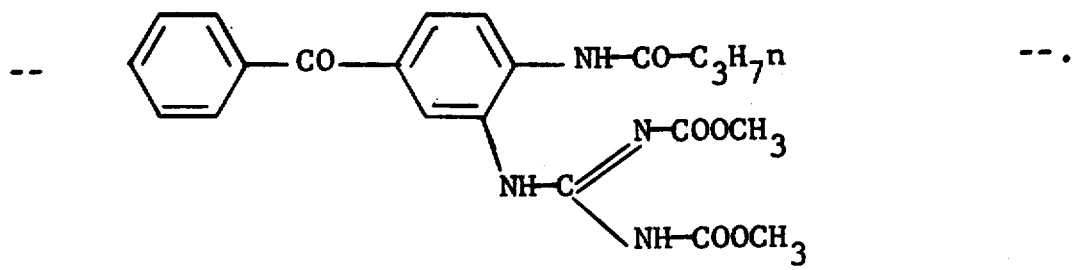

UNITED STATES PATENT AND TRADEMARK OFFICE
CERTIFICATE OF CORRECTION

PATENT NO. : 3,950,395
DATED : April 13, 1976
INVENTOR(S) : HEINRICH KOLLING ET AL Page 3 of 3

It is certified that error appears in the above-identified patent and that said Letters Patent are hereby corrected as shown below:

Columns 33 and 34, second structural formula should read:

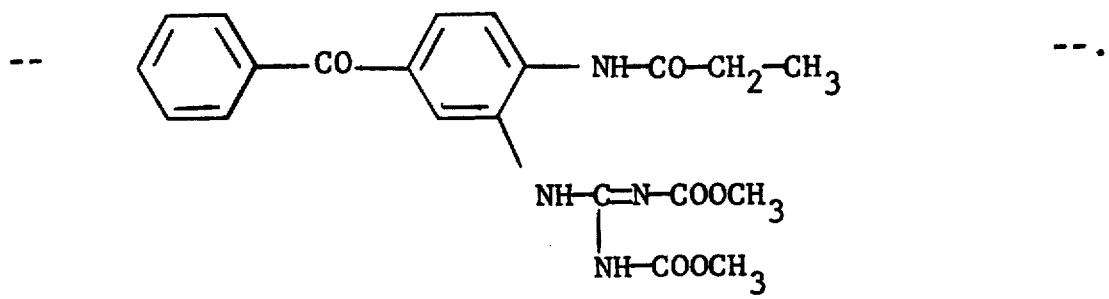

Column 40, line 44, after "and", there should be a new paragraph as follows:

--Z is $OR^1$ wherein $R^1$ is as above defined;

hydrogen; alkyl of 1 to 18 carbon --.

This certificate supersedes Certificate of Correction issued August 31, 1976.

Signed and Sealed this

Twenty-eighth Day of December 1976

[SEAL]

Attest:

RUTH C. MASON
Attesting Officer

C. MARSHALL DANN
Commissioner of Patents and Trademarks